United States Patent [19]
Russell

[11] 3,930,414
[45] Jan. 6, 1976

[54] METHOD AND APPARATUS FOR OBTAINING A REPRESENTATIVE SAMPLE OF FLUID FLOWING THROUGH A CONDUIT

[75] Inventor: Jolly T. Russell, Liberal, Kans.

[73] Assignee: Panhandle Eastern Pipe Line Co., Houston, Tex.

[22] Filed: Oct. 2, 1973

[21] Appl. No.: 402,846

[52] U.S. Cl.............................. 73/422 R
[51] Int. Cl.².......................... G01N 1/14
[58] Field of Search.......... 73/198, 422 R, 421.5 R; 137/100, 101, 101.9

[56] References Cited
UNITED STATES PATENTS

| | | | |
|---|---|---|---|
| 2,245,679 | 6/1941 | Kelley | 73/422 R |
| 3,794,909 | 2/1974 | Smith | 73/28 |

FOREIGN PATENTS OR APPLICATIONS

| | | | |
|---|---|---|---|
| 668,227 | 8/1963 | Canada | 73/422 R |

*Primary Examiner*—S. Clement Swisher
*Attorney, Agent, or Firm*—Jennings B. Thompson

[57] ABSTRACT

A flow restriction is placed in the pipeline through which the fluid to be sampled flows to provide a pressure drop that is proportional to the rate of flow of the fluid in the line. A sample bottle is connected to the line through a sample conduit that also contains a flow restriction to cause a pressure drop in the fluid flowing to the sample bottle. A variable flow restriction in the sample line downstream of the first flow restriction is adjusted to maintain the pressure drop across the flow restriction in the sample line proportional to the pressure drop across the flow restriction in the pipeline so that fluid flows into the sample bottle at a rate that is proportional to the rate of flow of fluid in the pipeline.

4 Claims, 1 Drawing Figure

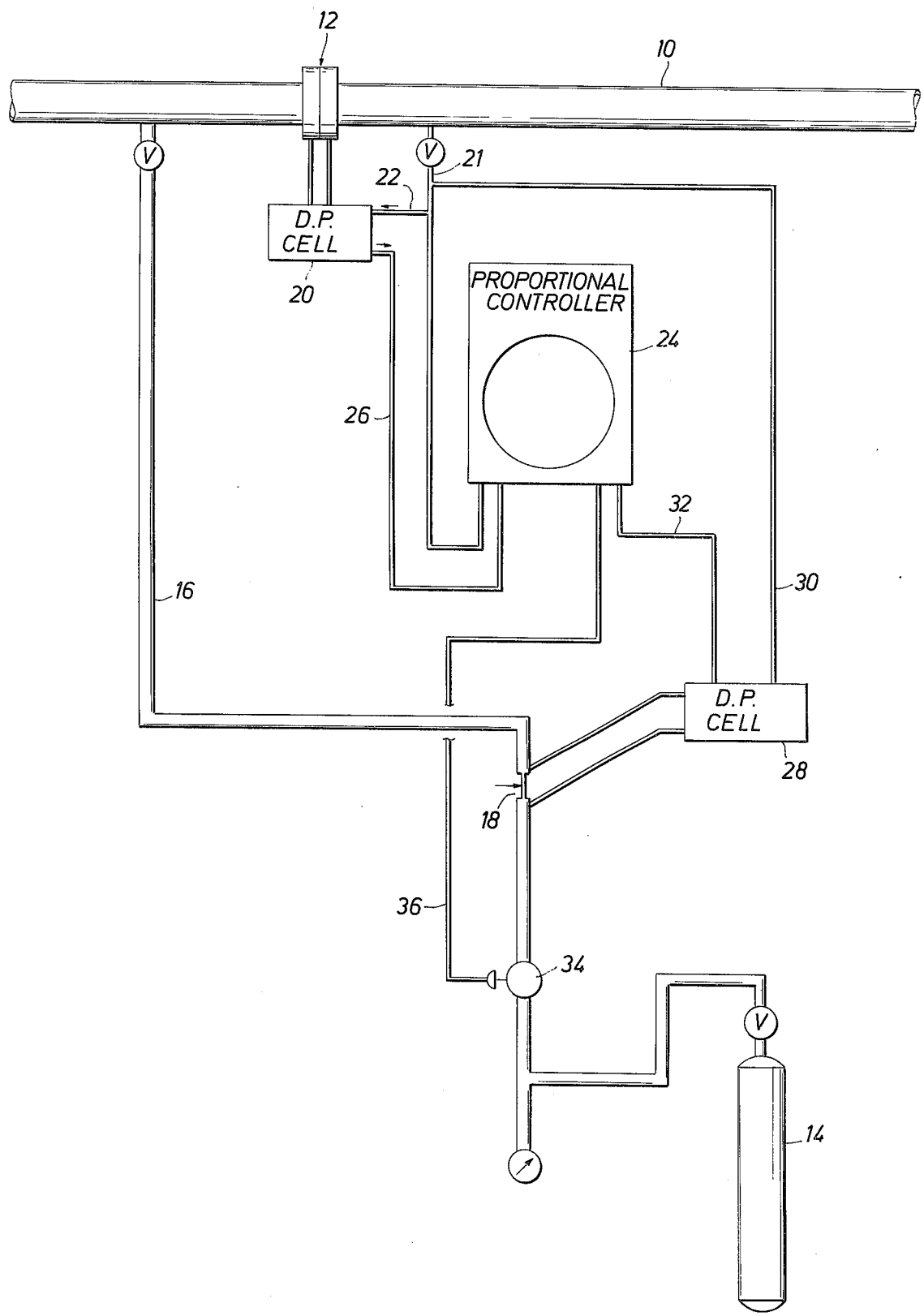

METHOD AND APPARATUS FOR OBTAINING A REPRESENTATIVE SAMPLE OF FLUID FLOWING THROUGH A CONDUIT

This invention relates to a method of and apparatus for obtaining a representative sample of fluid flowing through a conduit during a given period of time.

There are many occasions where it is important to know the composition of fluid flowing through a pipeline as well as the volume. For example, natural gas is often traded between companies. More and more this is being done on an energy rather than a volume basis. Spot samples to determine the energy content are satisfactory if the composition of the gas is fairly constant. Where it varies, however, it is very important to have a representative sample of the gas delivered.

Also, it is common practice to measure the volume of gas flowing through a pipeline with an orifice meter. The formula used includes values for the specific gravity and supercompressibility of the gas. These are determined from samples and therefore good representative samples are important.

It is particularly important to obtain representative samples where gas is passed through a plant to have certain constituents removed, such as ethane and propane. The ability of these plants to remove these constituents varies with throughput and therefore the makeup of the tail gate gas may vary substantially during a given period of time. It is important that a representative sample of this gas be obtained so that the seller and the buyer know what they are exchanging.

Therefore, there is a need for a method and apparatus for obtaining a representative sample of fluid flowing through a pipeline over a given period of time, and it is an object of this invention to provide such method and apparatus.

It is a further object of this invention to provide a method of and apparatus for obtaining a representative sample of fluid flowing through a pipeline during a preselected period of time.

It is a further object of this invention to provide a method of and apparatus for obtaining a representative sample of the fluid that passed through a pipeline during a period of time by causing the sample to flow into the sample bottle continuously during said period at a rate that is proportional to the rate of flow of fluid in the pipeline.

These and other objects, advantages, and features of this invention will be apparent to those skilled in the art from a consideration of this specification, including the attached drawing and appended claims.

In the drawing, the preferred embodiment of the apparatus of this invention is shown arranged to obtain a representative sample of a fluid, such as natural gas, flowing in pipeline 10. In accordance with this invention, the flow through pipeline 10 is restricted by a flow restriction, such as orifice plate assembly 12. Sample bottle 14 is connected to pipeline 10 through conduit 16 upstream of orifice plate assembly 12. A flow restriction is provided in conduit 16, indicated in the drawing by the number 18. This flow restriction is shown schematically as being fixed in size, however in practice, a variable restriction of one type or another will be used at this point in the sample line. For example, an adjustable needle valve would be satisfactory.

In accordance with this invention, means are provided to measure the pressure drop across the flow restriction in the pipeline, and to also measure the pressure drop across the flow restriction in the sample line. Means are also provided responsive to the two pressure drops to control the pressure drop across the flow restriction in the sample line so that the rate of flow into the sample bottle through this flow restriction is proportional to the rate of flow through the pipeline.

In the embodiment shown, differential pressure cell 20 is supplied with instrument pressure through lines 21 and 22. This cell provides a pressure signal to proportional controller 24 through line 26 that is proportional to the pressure drop across orifice 12. In the same manner, differential pressure cell 28 is provided with instrument air through lines 21 and 30 and provides an output signal to proportional controller 24 through line 32 that is proportional to the pressure drop across flow restriction 18. The proportional controller, in turn, provides a pressure signal to motor valve 34 through line 36 that operates to vary the opening through motor valve 34 so as to maintain the pressure signals received through lines 26 and 32 in a preselected relationship. By maintaining such a relationship, the rate of flow of fluid through flow restriction 18 will be proportional to the flow through orifice 12. Consequently, a representative sample of the fluid flowing in the line during a given period will be collected in sample bottle 14.

For example, assume the pressure upstream of orifice plate assembly 12 to be 1,000 p.s.i. The pressure upstream of restriction 18 in the sample conduit is also 1,000 p.s.i. At the beginning, the pressure in the sample bottle is usually less than atmospheric since the bottle is preferably evacuated before use. If the sample is to be taken over a period of several hours, such as twenty four, then pressure build up in the bottle must be relatively slow. If the pressure drop across the orifice in the pipeline is 40 p.s.i. for example, the pressure drop across flow restriction 18 may be maintained the same or some percentage thereof. If the same, then motor valve 34 must maintain the pressure downstream of flow restriction 18 at 960 p.s.i. when the upstream pressure is 1,000 p.s.i. If the rate of flow decreases, the pressure drop across orifice assembly 12 will drop. This will cause proportional controller 24 to adjust valve 34 to change the pressure drop across restriction 18 by the same amount to keep the rate of flow to the bottle proportional to the rate of flow in the pipeline.

Flow restriction 18, of course, must be such that sample bottle 14 will not reach pipeline pressure during the period of time that the sample is to be taken. In other words, there must be always a flow through flow restriction 18 sufficient to provide the necessary pressure drop to cause fluid to flow into the sample bottle and to allow motor valve 34 to maintain the necessary pressure drop. Therefore, for longer time periods, flow restriction 18 must be adjusted to reduce the flow to the sample bottle. In addition, the proportional controller can be adjusted to maintain the pressure drop across flow restriction 18 at a percentage, say one-half, the pressure drop across orifice assembly 12. This will further reduce the volume flowing to the sample bottle, but will allow each unit volume of fluid flowing through the pipeline to be represented in the sample bottle.

If the pipeline is carrying a mixture, such as natural gas, that may contain constitutents that may condense when cooled, the apparatus should be heated to keep condensate from collecting downstream of flow restriction 18 and valve 34.

From the foregoing, it will be seen that this invention is one well adapted to attain all of the ends and objects hereinabove set forth, together with other advantages which are obvious and which are inherent to the method and apparatus.

It will be understood that certain features and subcombinations are of utility and may be employed without reference to other features and subcombinations. This is contemplated by and is within the scope of the claims.

As many possible embodiments may be made of the apparatus and method of this invention without departing from the scope thereof, it is to be understood that all matter herein set forth or shown in the accompanying drawings is to be interpreted as illustrative and not in a limiting sense.

The invention having been described, what is claimed is:

1. A method of obtaining a representative sample of fluid flowing through a pipeline comprising the steps of connecting a sample bottle to the pipeline through a flow restriction through which fluid can flow from the pipeline into the sample bottle, measuring the pressure drop across a restriction in the pipeline, measuring the pressure drop across a flow restriction through which the fluid flows to the sample bottle and maintaining the pressure drop across the flow restriction through which the fluid flows to the sample bottle a proportional amount of the pressure drop across the flow restriction in the pipeline to cause the fluid to flow into the sample bottle at a rate proportional to the rate of flow of fluid in the pipeline.

2. Apparatus for obtaining a representative sample of a fluid flowing through a conduit comprising means restricting the flow of fluid through the conduit to provide a pressure drop proportional to the rate of flow of fluid through the conduit, a sample bottle, a sample conduit connecting the sample bottle to the fluid conduit, means restricting the flow of fluid through the sample conduit to the sample bottle to provide a pressure drop across the flow restriction proportional to the rate of flow of fluid to the sample bottle and means for maintaining the rate of flow of fluid to the sample bottle proportional to the rate of flow of fluid through the fluid conduit to obtain a continuous flow of fluid into the sample bottle at a rate proportional to the rate of flow of fluid in the conduit said means for maintaining the rate of flow to the sample bottle including means for measuring the pressure drop across the flow restricting means in the fluid conduit, means for measuring the pressure drop across the flow restricting means in the sample conduit, and means responsive to the pressure drops to control the flow of fluid through the sample conduit to maintain the rate the fluid flows into the sample bottle proportional to the rate of flow of fluid in the fluid conduit.

3. Apparatus for obtaining a representative sample of a fluid flowing through a conduit during a preselected period of time comprising a bottle for collecting the sample, a conduit connecting the sample bottle to the fluid conduit, a flow restriction in the fluid conduit, a flow restriction in the sample conduit to restrict the flow of fluid through the sample conduit sufficiently to keep the pressure downstream of the flow restriction from reaching the pressure of the fluid in the fluid conduit, means for measuring the pressure drop across each flow restriction and means responsive to the two pressure drops to maintain the pressure drop across the restriction in the sample conduit a proportional amount of the pressure drop across the flow restriction in the fluid conduit to cause the fluid to flow into the sample bottle at a rate proportional to the rate of flow of fluid in the fluid conduit.

4. The apparatus of claim 3 in which the means responsive to the two pressure drops includes a second flow restriction in the sample conduit downstream of the first mentioned flow restriction in the sample conduit and means to vary the second flow restriction to maintain the pressure drop across the upstream sample conduit flow restriction proportional to the pressure drop across the flow restriction in the fluid conduit.

* * * * *